US007742802B2

(12) United States Patent
Green, II et al.

(10) Patent No.: US 7,742,802 B2
(45) Date of Patent: Jun. 22, 2010

(54) SYSTEM FOR DETERMINING A POSITION OF A POINT ON AN OBJECT

(75) Inventors: John Michael Green, II, Lincoln Park, NJ (US); Jose Luis Moctezuma de la Barrera, Freiburg (DE)

(73) Assignee: Howmedica Osteonics Corp., Mahwah, NJ (US)

( * ) Notice: Subject to any disclaimer, the term of this patent is extended or adjusted under 35 U.S.C. 154(b) by 593 days.

(21) Appl. No.: 10/798,677

(22) Filed: Mar. 11, 2004

(65) Prior Publication Data

US 2005/0199250 A1     Sep. 15, 2005

(51) Int. Cl.
    *A61B 5/05*         (2006.01)
(52) U.S. Cl. ...................................... 600/424
(58) Field of Classification Search ................ 600/594, 600/587, 409, 437, 443, 447, 459; 128/898
    See application file for complete search history.

(56) References Cited

U.S. PATENT DOCUMENTS

| 4,826,492 | A | * | 5/1989 | Magasi | 604/274 |
| 5,321,257 | A | * | 6/1994 | Danisch | 250/227.16 |
| 5,449,356 | A | * | 9/1995 | Walbrink et al. | 606/49 |
| 5,617,857 | A | | 4/1997 | Chader et al. | 128/653.1 |
| 5,633,494 | A | | 5/1997 | Danisch | 250/227.16 |
| 5,665,092 | A | | 9/1997 | Mangiardi et al. | 606/86 |
| 5,917,180 | A | | 6/1999 | Reimer et al. | 250/227.14 |
| 6,073,043 | A | | 6/2000 | Schneider | 600/424 |
| 6,127,672 | A | | 10/2000 | Danisch | 250/227.14 |
| 6,338,716 | B1 | | 1/2002 | Hossack et al. | 600/459 |
| 6,390,982 | B1 | * | 5/2002 | Bova et al. | 600/443 |
| 6,511,427 | B1 | * | 1/2003 | Sliwa et al. | 600/438 |
| 6,524,260 | B2 | * | 2/2003 | Shechtman et al. | 600/594 |
| 6,563,107 | B2 | | 5/2003 | Danisch et al. | 250/227.14 |
| 6,676,706 | B1 | | 1/2004 | Mears et al. | 623/22.4 |
| 6,746,402 | B2 | * | 6/2004 | Ustuner | 600/462 |
| 7,072,707 | B2 | * | 7/2006 | Galloway et al. | 600/424 |
| 7,141,019 | B2 | * | 11/2006 | Pearlman | 600/437 |
| 2003/0198372 | A1 | * | 10/2003 | Touzawa et al. | 382/128 |

FOREIGN PATENT DOCUMENTS

| WO | WO 2004/073495 | 9/2004 |
| WO | WO 2004/073543 | 9/2004 |

OTHER PUBLICATIONS

Amin et al."Ultrasound Registration of the Bone Surface for Surgical Navigation," (Biomedical Paper, Computer Aided Surgery) 8:1-16 (2003), (16 pages).
Amstutz et al. "A-Mode Ultrasound-Based Registration in Computer-Aided Surgery of the Skull," Arch Otolaryngol Head Neck Surg, vol. 129, Dec. 2003, (pp. 1310-1316).

* cited by examiner

*Primary Examiner*—Brian Casler
*Assistant Examiner*—Elmer Chao
(74) *Attorney, Agent, or Firm*—McCracken & Frank LLP

(57) ABSTRACT

A system and method are disclosed for determining a global position of an anatomical structure. The system utilizes a surgical navigation system and a substrate that is capable of being removably mounted to an outer surface of a user's body. The substrate includes a positional device and a sensor that is tracked by the surgical navigation system. A finger mounted structure capable of communicating with the positional device is also provided. The concatenation of a position of the sensor and a position of the finger mounted structure allows a global position of a point on the anatomical structure to be determined by a computer system.

124 Claims, 8 Drawing Sheets

SYSTEM FOR DETERMINING A POSITION OF A POINT ON AN OBJECT

BACKGROUND

1. Technical Field

This invention relates generally to surgical navigation systems. More particularly, this invention relates to a substrate removably attached to a user that assists the user in determining the position of a point on an anatomical structure within a patient.

2. Background Art

The use of surgical navigation systems for assisting surgeons during surgery is quite common. Some systems are used to determine points of interest on organs or bony structures. Determining the precise location of a point on these anatomical structures has proved difficult. One typical surgical technique is to use rigid pointer devices, such as the one described in U.S. Pat. No. 5,617,857, with surgical navigation trackers attached thereto. These conventional systems, however, have numerous problems. Present systems suffer from pointer lift-off concerns, where the tip of the pointer that should correspond to the point desired to be located on the anatomical structure has moved away from the bony structure or organ when the location is determined. Other problems arise with conventional techniques when the anatomical structure is relatively inaccessible, especially to rigid pointers that cannot bend around obstructions within the patient to reach the anatomical structure. This is especially problematic with the increased use of smaller incisions for surgical procedures. Also of great importance is the wasted time surgeons must tolerate when switching from pointers to the other surgical tools needed to operate on the patient. The present invention provides a system for determining the global position of a point on an anatomical structure that does not suffer from the same lift-off, inaccessibility, or time wasting problems of conventional techniques.

SUMMARY OF THE INVENTION

One embodiment of the present invention is directed toward a system for determining a global position of an anatomical structure of a patient's body. The system includes a surgical navigation system. The system also includes a substrate adapted to be removably mounted to an outer surface of a user's body. A sensor is attached to the substrate that can be tracked by the surgical navigation system to determine a position of the sensor. A positional device is attached to the substrate. Further, the system includes a structure adapted to be mounted to a finger of the user. The structure is movable in relation to the sensor and adapted to be placed adjacent to a point on the anatomical structure. Additionally, the positional device is adapted to determine a relative position of the structure in relation to the positional device. Lastly, a first circuit is provided for calculating a global position of the point on the anatomical structure by concatenating the position of the sensor and the relative position of the structure.

A further embodiment of the present invention is directed toward a system for determining a global position of an object. The system includes a navigation system. The system also includes a substrate comprising a glove adapted to be mounted to an outer surface of a user's body. A sensor is attached to the substrate that can be tracked by the navigation system to determine a position of the sensor. Additionally, the system includes a positional device attached to the substrate. Further, the system includes a structure mounted to a finger of the glove. The structure is movable in relation to the sensor and is adapted to be placed adjacent to a point on the object. Additionally, the positional device is adapted to determine a relative position of the structure in relation to the positional device. Lastly, a first circuit is provided for calculating a global position of the point on the object by concatenating the position of the sensor and the relative position of the structure.

Another embodiment of the present invention is directed toward a method for determining a position of a point on an anatomical structure of a patient using a surgical navigation system. The method includes the step of providing a surgical navigation system. Another step includes mounting a substrate in a removable manner to an outer surface of a user's body, the substrate having a positional device and a sensor that can be detected by the surgical navigation system to determine a position of the sensor. A further step includes covering a fingertip of the user with a finger mounted structure. The finger mounted structure is movable in relation to the sensor. Additionally, the positional device is adapted to determine a relative position of the finger mounted structure with respect to the positional device. Lastly, the method includes the steps of placing the finger mounted structure on the point of the anatomical structure to be determined, calculating the relative position of the finger mounted structure in relation to the positional device, and determining a global position of the point by concatenating the position of the sensor and the relative position of the finger mounted structure.

A yet further embodiment of the present invention is directed toward a method for determining a position of a point on an object using a surgical navigation system. The method includes the step of providing a surgical navigation system. Another step includes mounting a glove on a user's hand, the glove having a positional device that determines a position of a point on the object and a sensor that can be detected by the surgical navigation system to determine a position of the sensor. Another step includes disposing the finger mounted structure on a finger of the glove capable of communicating with the positional device to determine a relative position of the structure in relation to the positional device. The finger mounted structure is movable in relation to the sensor. Lastly, the method includes the steps of placing the finger mounted structure on the point of the object to be determined and determining a global position of the point by concatenating the position of the sensor and the relative position of the structure.

A further embodiment of the present invention is directed toward a method for determining a position of a point on an anatomical structure through a small incision opening using a surgical navigation system. The point is obstructed from the incision. The method includes the step of providing a surgical navigation system. Another step includes mounting a substrate in a removable manner to an outer surface of a user's body. A further step includes covering a tip of the user's finger with a finger mounted pointer having a rigid tip. The finger mounted pointer is capable of communicating with an external positional device mounted on the substrate and the external positional device is associated with a sensor mounted on the substrate that can be detected by the surgical navigation system. Additionally, the finger mounted pointer is movable in relation to the sensor. Another step includes manipulating the finger mounted pointer so that the rigid tip is in contact with the point to be determined. Lastly, the method includes the steps of determining the relative position of the finger mounted pointer in relation to the sensor with the external positional device, determining the global position of the sensor, and determining the global position of the point by concatenating the relative position of the finger mounted pointer and the global position of the sensor.

Another embodiment of the present invention is directed toward an apparatus for determining a position of a point on an anatomical structure. The apparatus includes a surgical navigation system and a glove adapted to be mounted on a hand of a user. A sensor is attached to the glove that can be tracked by the surgical navigation system to determine a position of the sensor. A magnetic tracker is also attached to the glove. The apparatus also includes a structure comprising a magnetic sensor mounted to a finger of the glove. The magnetic sensor is movable in relation to the sensor and adapted to be placed adjacent to a point on the anatomical structure. The magnetic tracker determines a relative position of the magnetic sensor. The apparatus further includes a first circuit for calculating a global position of the point on the anatomical structure by concatenating the position of the sensor and the relative position of the magnetic sensor.

Other aspects and advantages of the present invention will become apparent upon consideration of the following detailed description.

DESCRIPTION OF THE PREFERRED EMBODIMENT(S)

Figure 1:
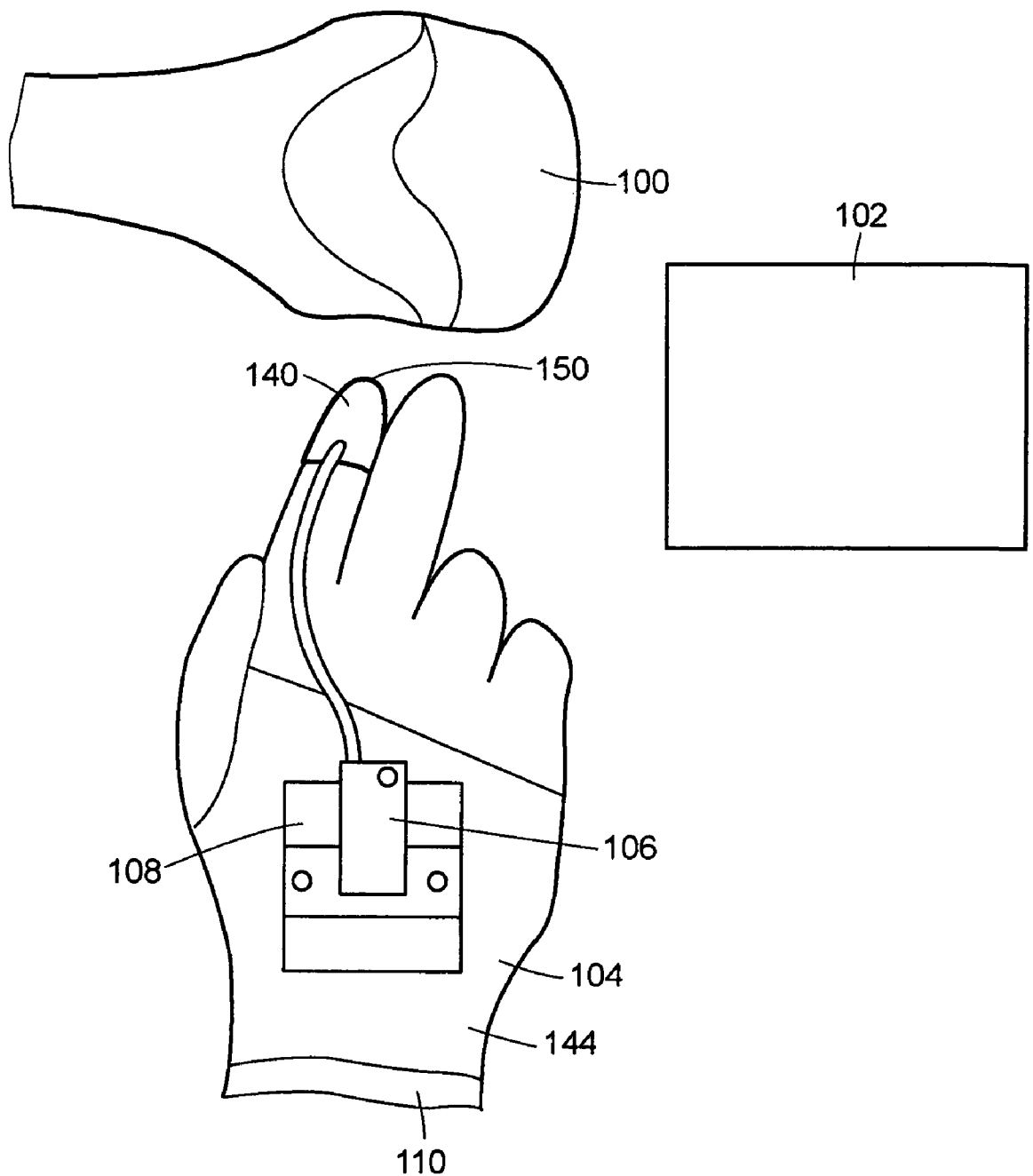
FIG. 1 is a top plan view of an embodiment of a substrate used with a finger mounted structure.

The present invention is directed toward a system for determining a position of a point on an anatomical structure 100. The system includes a navigation system (also known as a "surgical navigation system") 102 and a substrate 104. The substrate 104 includes a sensor 106 for interacting with the navigation system and a positional device 108 for determining the position of the anatomical structure 100. The substrate 104 is removably mounted to an outer surface 110 of a user's body. The structure and functioning of the surgical navigation system 102, the sensor 106, and the positional device 108 are disclosed in U.S. patent application Ser. No. 10/798,614, filed Mar. 11, 2004 (the application is entitled "System for Determining a Position of an Object," and was filed the same day as the instant application, the disclosure of which is herein incorporated by reference.

While the present invention has a variety of applications in many different fields, of particular importance are the embodiments that utilize the invention in surgical environments. The anatomical structure 100 will therefore typically be found in a patient's body. In a preferred embodiment of the present invention, the anatomical structure 100 is a bony structure. However, the anatomical structure 100 could also be an organ or any other structure found within the patient's body. It is also envisioned that embodiments of the present invention may be used to determine positions of points on objects outside of surgical applications. Therefore, any of the embodiments hereinafter mentioned in respect to the anatomical structure 100 may also be used with bony structures, organs, other structures within a patient's body, or any other object a user desires to find the position of a point on.

Figure 2:
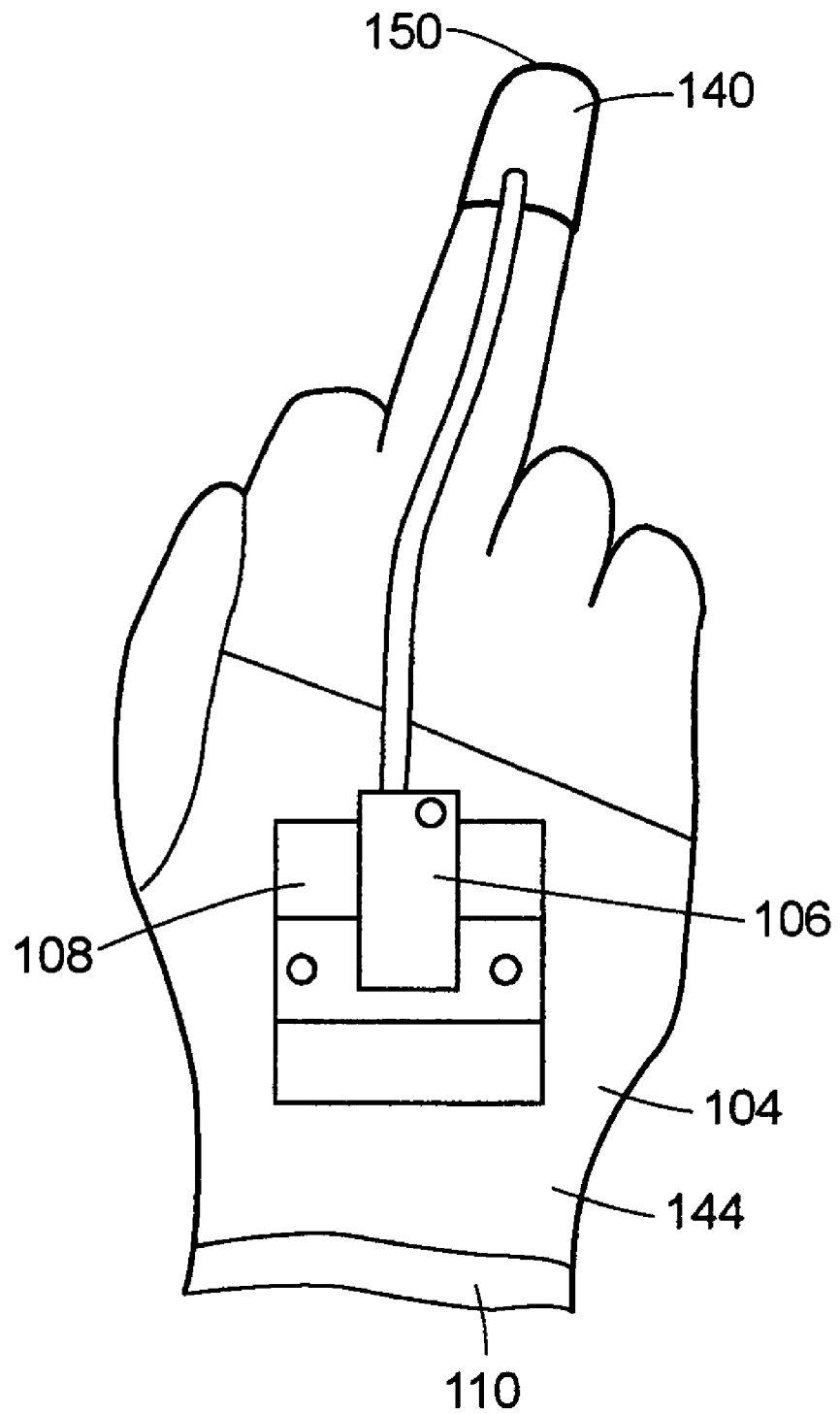
FIG. 2 is a top plan view of an embodiment similar to FIG. 1 with a finger mounted structure on a different finger.
Figure 2A:
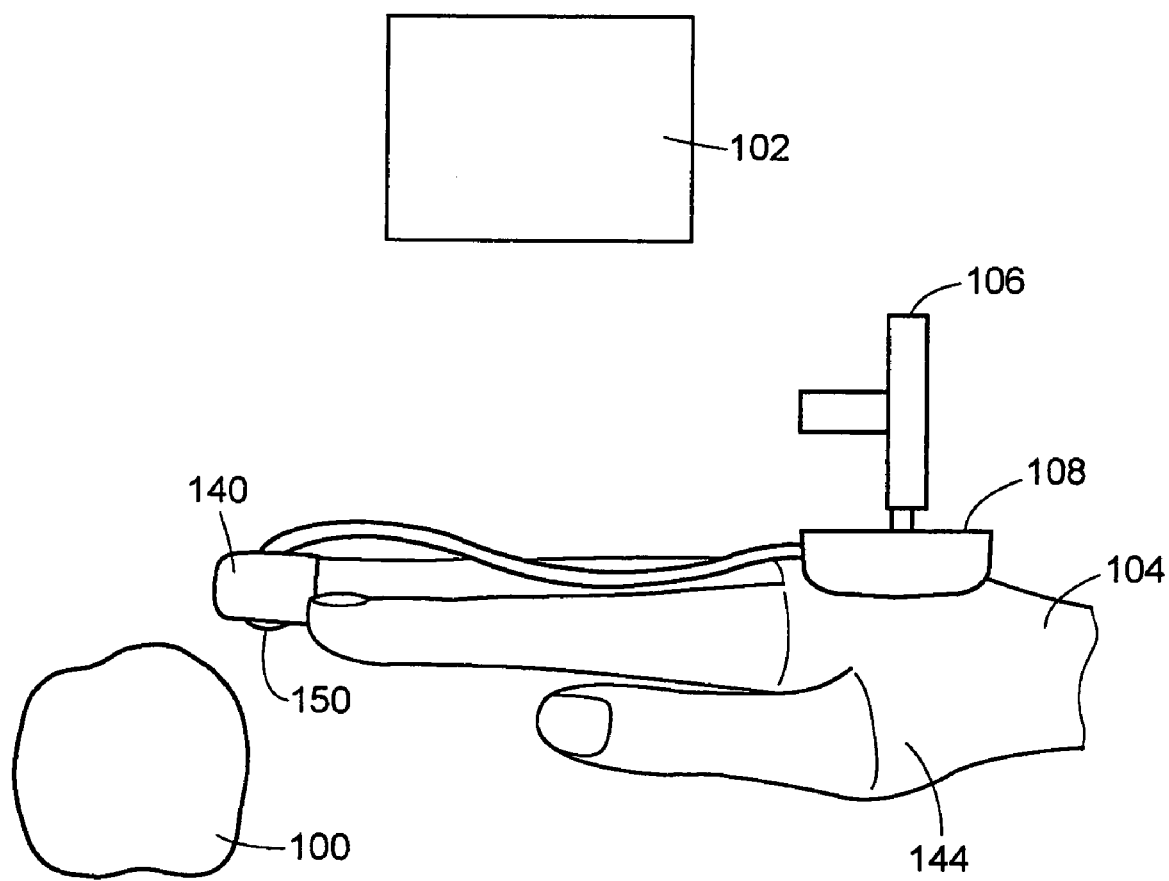
Figure 3:
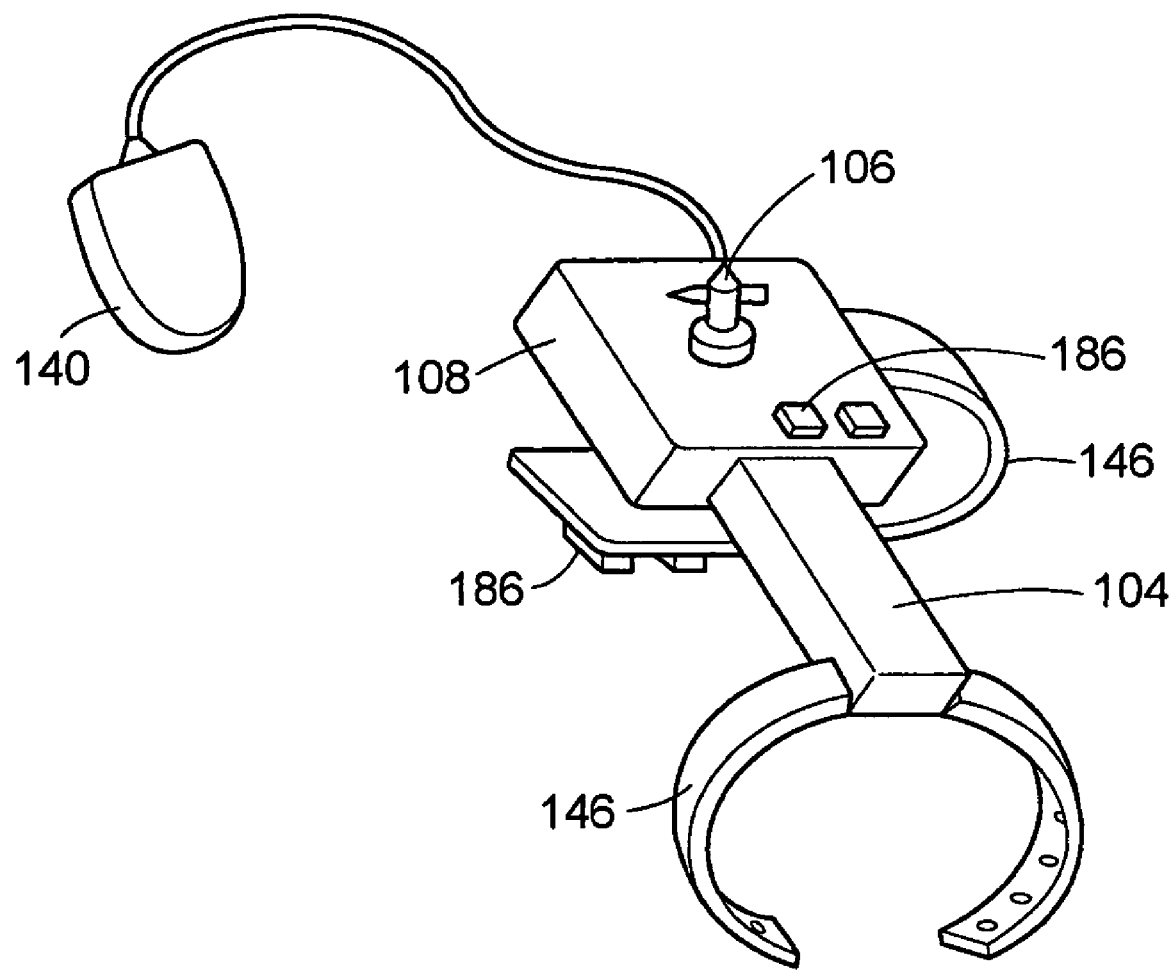
FIG. 3 is a an isometric view of an embodiment of another substrate with a finger mounted structure.

The invention as embodied in FIG. 1 comprises two distinct sections. One of the sections is a finger mounted structure 140 disposed on a finger of the user. In one embodiment, the finger mounted structure 140 is disposed on the index finger of the user. In another embodiment, depicted in FIGS. 2 and 2a, the finger mounted structure 140 is disposed on the middle finger to allow for greater reach. The second section is the substrate 104. In the present embodiment, the substrate 104 comprises a glove 144 disposed on the hand and wrist of the user. In some embodiments, the glove 144 of FIG. 1 could completely extend over the hand and/or wrist of the user, allowing the finger mounted structure 140 to be attached or in contact with the substrate 104. Other embodiments vary the degree of hand and wrist coverage to suit the needs and comfort of the user. FIG. 3 shows yet another embodiment of the present invention that utilizes clasp-like structures 146 to mount the substrate 104 on the user's hand and wrist. Similar clasping techniques, Velcro bands, adhesive material, or any other mounting structure known to those skilled in the art could be used to attach the substrate 104 to the outer surface 110 of the user's body.

While the present embodiment utilizes a single uniform substrate 104 that extends over a portion of the hand and wrist of the user, other embodiments may utilize non-uniform substrates with multiple components. It is also envisioned that other embodiments may use single or multiple component substrates 104 that extend over other areas of the outer surface 110 of the user's body, such as the arm or shoulder. Indeed, the substrate 104 could take on numerous forms that provide for user comfort and mobility. For example, the user may wish to have the sensor 106 attached to a discrete portion of the substrate 104 on the shoulder or back of the user, while the positional device 108 is disposed on another discrete portion of the substrate 104 on the arm or hand of the user. It is even possible that the positional device 108 can be temporarily attached to the patient at a point near the incision. The precise manner or number of elements that comprise the substrate 104 is variable depending on the user's needs and the environment.

The embodiment of the substrate 104 in FIG. 1 is constructed of a sufficiently flexible material so as not to greatly retard the movement of the user's hand. Those skilled in the art will know what materials can provide sufficient user maneuverability. While the present embodiment is constructed of a generally flexible material, other embodiments may use more rigid metallic or plastic composites to construct the substrate 104 with generally similar advantageous properties. FIG. 3 shows clasp-like structures 146 that could be comprised of more rigid materials, but still would allow for good mobility of the user's hand. The present embodiment also has the added advantage of allowing the user to have the substrate 104 removably attached to the outer surface 110 of the user's body during use. The advantage of such a system may be realized in a surgical environment where a surgeon may need to use a surgical tool and also find the position of a point on an anatomical structure 100. The unobtrusiveness of the present embodiment allows the surgeon to garner point positional data while simultaneously holding or using another surgical tool. The surgeon no longer has to free up a hand by putting down the surgical tool and wasting valuable time.

As noted above, the substrate 104 is removably mounted to the outer surface 110 of the user's body. In the embodiments depicted in FIGS. 1-3, the sensor 106 and the positional device 108 are disposed on a portion of the substrate 104 closer to the back of the user's hand than the palm of the user's hand. However, various other embodiments dispose the sensor 106 and the positional device 108 in different manners on the substrate 104. In all embodiments, the sensor 106 should be positioned to allow communication between itself and the surgical navigation system 102. The positional device 108 must also be oriented to allow communication with the surgical navigation system 102, or, must be allowed to communicate with the sensor 106. Those skilled in the art will know how to relay the information between the various components.

In all embodiments, the sensor 106 or the positional device 108 may be fixedly attached to the substrate 104, or be detachable from the substrate 104. It is also envisioned that all of the other components of the present system may be interchangeable to suit the user's needs. Differently sized substrates 104 may be provided to suit the variable sizes of the outer surface 110 of the user's body. Such variations may include differently sized gloves 144. The finger mounted structure 140 may also be of varying size to accommodate differences in user finger length and width.

As previously mentioned, embodiments of the present invention also include a finger mounted structure 140 disposed on the finger 142 of the user. In use, the finger mounted structure 140 is placed adjacent a point on the anatomical structure 100 to determine a position of the point. The finger mounted structure 140 is capable of communicating with the positional device 108. By manipulating the finger mounted structure 140 adjacent to the anatomical structure 100 such as depicted in FIG. 1, the position of the point on the anatomical structure 100 relative to the sensor 104 is determined. In some embodiments, the position of the finger mounted structure 140 that corresponds to the point on the anatomical structure 100 is a position of a tip 150 on the finger mounted structure 140. The tip 150 could be located adjacent to a tip of the user's finger, adjacent to a pad of the user's finger, or anywhere along the length of the finger mounted structure 140. The tip 150 may also protrude from the finger mounted structure 140, as may be seen in FIG. 2a, or be relatively flat against the finger mounted structure 140, as may be seen in FIG. 2. By concatenating the positional information of the point on the anatomical structure 100 from the positional device 108 and the position of the sensor 106, a global position for the point on the anatomical structure 100 is ascertained. The global position of the point may be displayed in numerous manners as known to those skilled in the art, including using a display monitor (not shown).

It is also envisioned that the anatomical structure 100 may be mapped using the present embodiment of the invention. The finger mounted structure 140 may be disposed in, or adjacent to, an anatomical structure 100 that is desired to be mapped. The user then manipulates his finger, and the corresponding finger mounted structure 140, along the area to be mapped. If the positional device 108 has been activated, the positional device 108 will be able to accumulate data on the position of a plurality of points on the anatomical structure 100. These discrete positions of points, measured relative to the sensor 106, may be concatenated with the respective sensor positional information and compiled to create a cloud point map of the anatomical structure 100.

The finger mounted structure 140 is also flexible enough to enable the finger mounted structure 140 to reach a point on the anatomical structure 100 that is obstructed from view or hard to reach. In many instances, surgeons are required to determine the position of points on anatomical structures 100 that are obstructed by foreign and non-foreign material with the patient's body. Typical rigid pointers used to determine positional information are not adequate in such scenarios. The present embodiment of the invention allows for the user to manipulate his finger, along with the finger mounted structure 140, to gain access to obstructed or hard to reach positions. The present embodiments also allow tactile feedback to the user to make the user aware of when he is touching the desired point on the anatomical structure 100. In many instances, surgeons using conventional pointers have taken inaccurate positional data because they took positional information at a point not touching the anatomical structure 100. This problem is obviated by allowing the user to feel where the anatomical structure 100 is and thereafter activate the positional device 108 at the appropriate time.

It is envisioned that in some embodiments, whether the user is seeking an obstructed or unobstructed point on the anatomical structure, the user will be able to reach the point through an incision in the patient's body that has a length less than 10 centimeters. In a more preferred embodiment, the user can gain access to the point on the anatomical structure within the patient's body with an incision length less than 5 centimeters. In a most preferred embodiment, the user gains access to the point on the anatomical structure through an incision length within the range of about 2.5 centimeters to about 5 centimeters. While the present embodiments have application in a wide variety of situations, including trauma scenarios where incisions may not be necessary, the relatively small incision size benefits the patient by offering a less invasive procedure. Indeed, the present embodiments may have great application in surgery involving the knees, hips, shoulders, elbows, or spine of a patient where the small incision size and relative flexibility of the finger mounted structure 140 are particularly advantageous.

Figure 4:
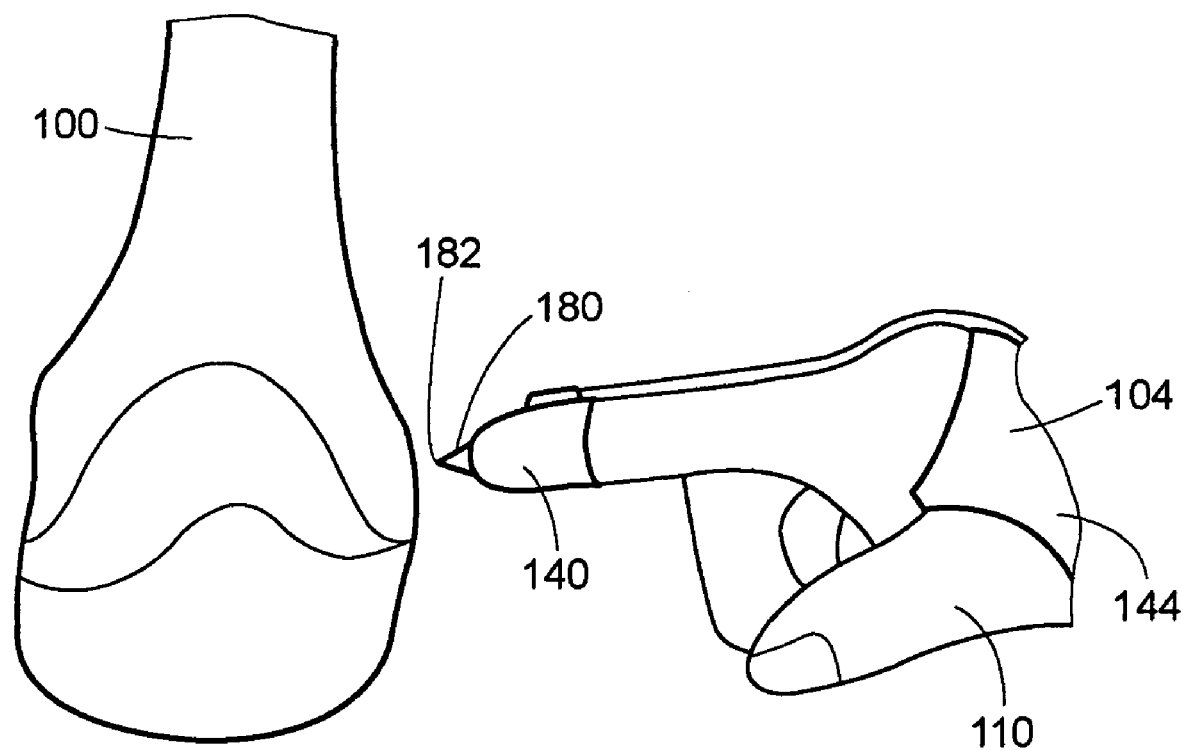
FIG. 4 is a perspective view of an embodiment of the substrate and finger mounted structure similar to the one seen in FIG. 1.
Figure 5:
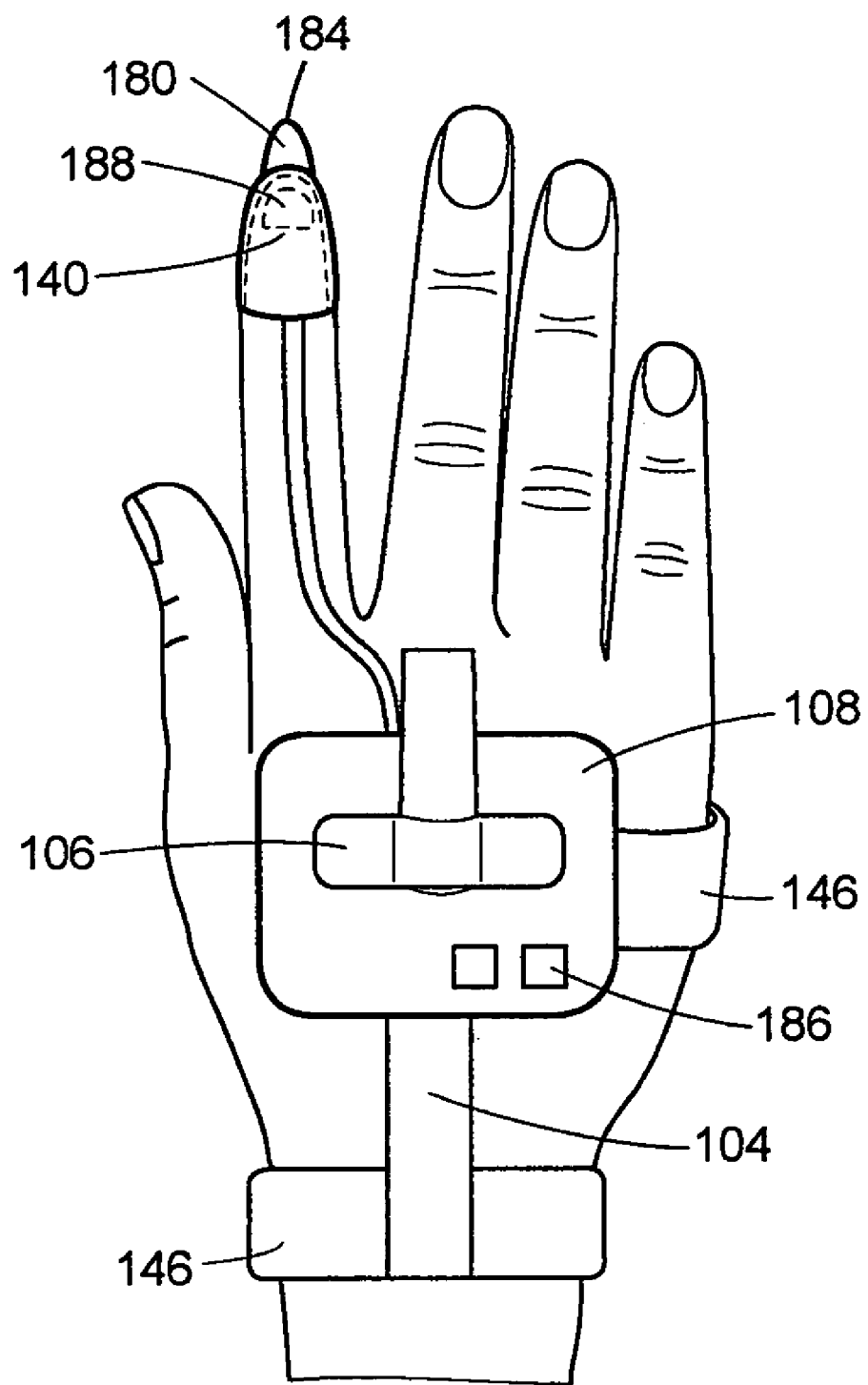
FIG. 5 is a top plan view of a substrate and finger mounted structure similar to the one seen in FIG. 3.

In some embodiments of the present invention, as seen in FIG. 4, the finger mounted structure 140 comprises a finger mounted pointer 180. The finger mounted pointer includes a rigid tip 182, which is placed adjacent the point on the anatomical structure 100 that the user wishes to find the position of. In some embodiments, as seen in FIG. 5, the finger mounted pointer 180 includes a depressible tip 184 that depresses when pressure is applied to it. In either embodiment, the position of the finger mounted structure 140 that corresponds to the position of the anatomical structure could be the depressible tip 184 or the rigid pointer 182. Typically, adequate pressure to depress the depressible tip 184 will result when the user pushes the depressible tip 184 against the point on the anatomical structure 100 he wishes to find the position of. In some embodiments, the depressible tip 184 acts as a switch to activate the positional device 108 to determine the position of the point on the anatomical structure 100. When the depressible tip 184 is pressed against the anatomical structure 100, it could be configured to take single, multiple, or continuous point determinations, and could also be configured to turn off when un-depressed. It is also envisioned that a transducer 188, shown in phantom, may be provided within the depressible tip that will activate the positional device 108 when a certain pressure value is reached. The user or a computer program could define the pressure value and adjust the pressure tolerance in light of the particular anatomical structure to be located. Other embodiments may utilize switches located on the substrate 104 to activate the positional device 108. FIG. 3 shows the substrate 104 with a switch 186 located on various areas of the substrate 104. Other embodiments only have one switch 186 located on the substrate 104. The same switches 186, or switches disposed in similar areas on the substrates 104 as those shown in FIG. 3, may be used to activate the sensor 106 or the surgical navigation system 102 in yet other embodiments. The location of the switch 186 can either be on the back of the hand as shown in FIG. 3 or located in the palm of the hand so that the switch can be activated by another finger on the same hand. The use of the switch 186 can ensure that the device is activated when the pointer 182 is in the proper position. Other embodiments envision a device that constantly supplies a stream of positional data whenever the positional device 108 is operational. The transducer 188 can cooperate with software to define the limit or value of pressure to be applied so as to assist in the accurate positioning of non-rigid internal anatomical structures such as organs.

Figure 6:
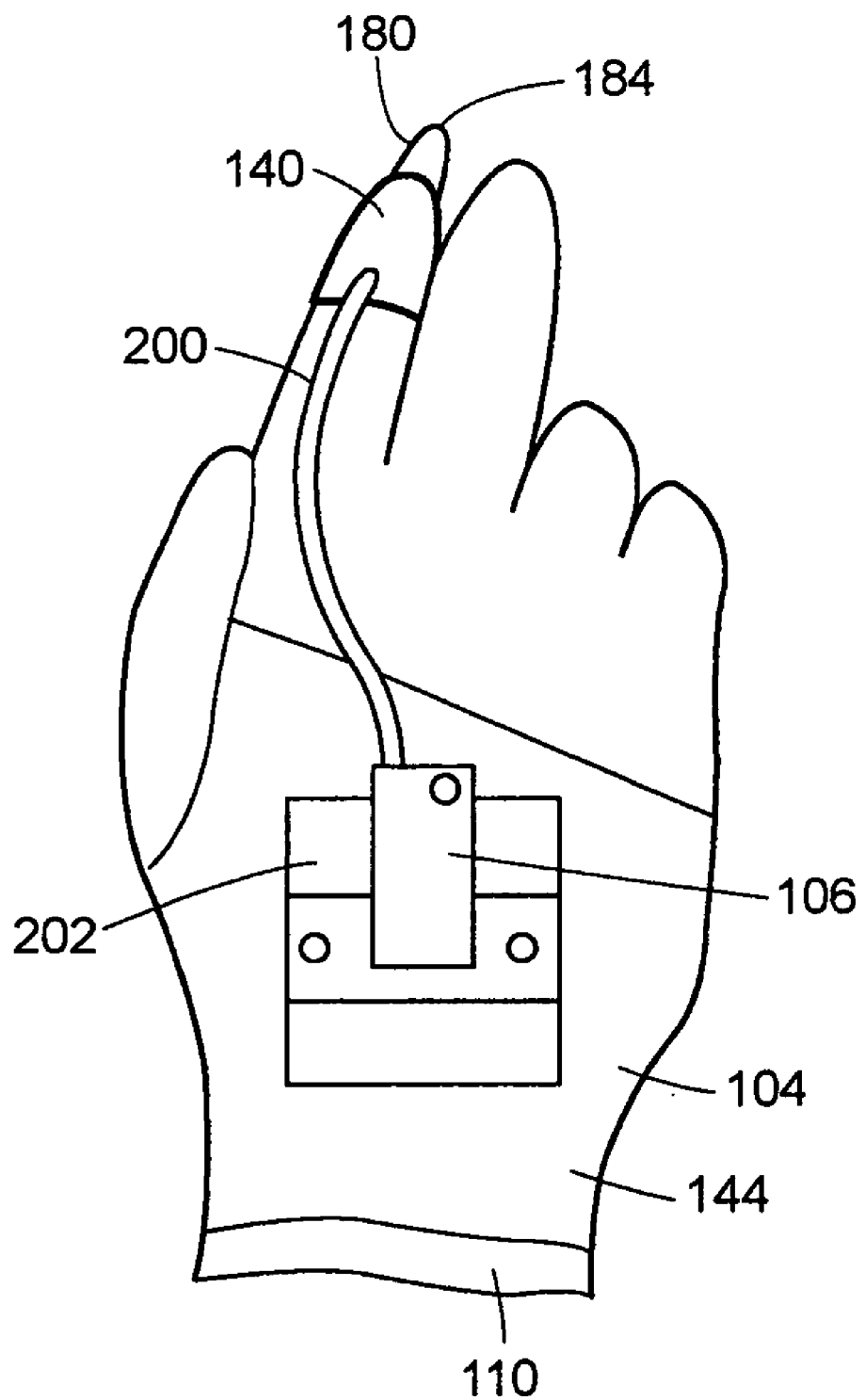
FIG. 6 is a top plan view of an embodiment similar to the one seen in FIG. 1 that uses a fiber optic device.

FIG. 6 shows another embodiment of the present invention, which has the finger mounted structure 140 connected to the substrate 104 by at least one fiber 200. The substrate 104 includes a fiber optic device 202 and the sensor 106, wherein there is a known relationship between the fiber optic device 202 and the sensor 106. The fiber 200 includes at least one bending sensor. As such, the bending sensors allow the user to determine the position of a point on the finger mounted structure 140 and relay this information to the fiber optic device 202. The point is preferably on the rigid tip 182 of the finger mounted pointer 180 or the depressible tip 184. By manipulating the finger mounted structure 140 adjacent to an anatomical structure 100, such as depicted in FIGS. 1 and 5, the position of the point on the anatomical structure 100 relative to the sensor 106 is determined. By concatenating the positional information from the fiber optic device 202 and the sensor 106, a global position for the point on the anatomical structure 100 is ascertained.

Figure 7:
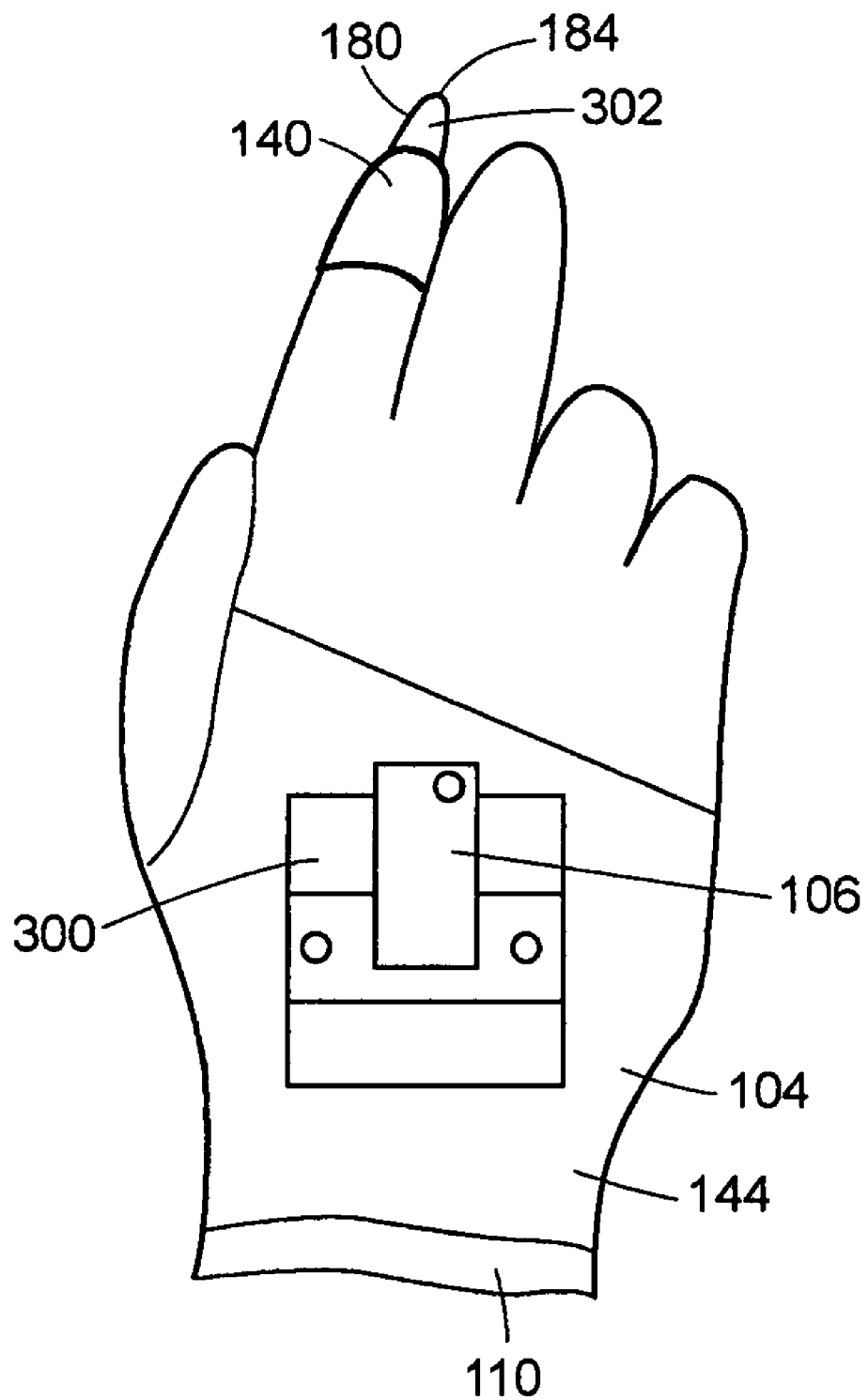
FIG. 7 is a top plan view of an embodiment similar to the one seen in FIG. 1 that uses a magnetic tracker.

It is also envisioned that the substrate 104 mounted in a removable fashion to the outer surface 110 of the user's body could be utilized in conjunction with a magnetic tracker 300. As may be seen in FIG. 7, an embodiment utilizing a magnetic tracker 300 could be used in a similar manner and incorporate similar structure as that discussed above in accordance with the fiber optic device 202. In the present embodiment, a magnetic tracker 300 is disposed on the on the substrate 104 and has a known relationship with the sensor 106. The finger mounted structure 140 contains a magnetic sensor 302, which is in communication with the magnetic tracker 300. The magnetic sensor 302 is preferably disposed on or near the rigid tip 182 of a finger mounted pointer 180 or on the depressible tip 184. In use, data from the magnetic sensor 302 corresponding to the position of the point on the anatomical structure 100 relative to the sensor 106 is relayed to the magnetic tracker 300. By concatenating the positional information of the sensor 106 and the magnetic tracker 300, a global position of the point on the anatomical structure 100 may be determined.

It is also envisioned that the present embodiments may have applications outside of the surgical field. A substrate 104 mounted to the outer surface 110 of a user's body could be used in a variety of situations. Indeed, it is envisioned that embodiments could be used in any situation that calls for the precise determination of the position of a point on an object.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A system for determining a global position of an anatomical structure of a patient's body, comprising:
   a surgical navigation system;
   a substrate adapted to be removably mounted to an outer surface of a user's body;
   a sensor attached to the substrate that can be tracked by the surgical navigation system to determine a position of the sensor;
   a positional device attached to the substrate;
   a structure adapted to be mounted to a finger of the user, wherein the structure is movable in relation to the sensor and the structure is adapted to be placed adjacent to a point on the anatomical structure, and wherein the positional device is adapted to determine a relative position of the structure in relation to the positional device; and
   a first circuit for calculating a global position of the point on the anatomical structure by concatenating the position of the sensor and the relative position of the structure.

2. The system of claim 1, wherein a second circuit is provided for displaying the global position of the point on the anatomical structure.

3. The system of claim 1, wherein the structure is attached to the substrate and the substrate is sufficiently flexible to enable the structure to reach a point on the anatomical structure that is obstructed from view.

4. The system of claim 1, wherein tactile feedback to the user aids the user in maneuvering the structure so that a position of the structure correlates to the point on the anatomical structure.

5. The system of claim 1, wherein the substrate comprises a glove and the structure comprises a fingertip of the glove.

6. The system of claim 1, wherein the structure comprises a pointer.

7. The system of claim 6, wherein the pointer includes a depressible tip.

8. The system of claim 7, wherein depressing the depressible tip activates the positional device.

9. The system of claim 8, wherein the depressible tip includes a transducer for activating the positional device when a defined pressure value is met.

10. The system of claim 7, wherein a position of the structure that correlates to the point on the anatomical structure is a position of the depressible tip.

11. The system of claim 1, wherein a position of the structure that correlates to the point on the anatomical structure is a position of a tip of the structure.

12. The system of claim 11, wherein the tip of the structure is located at a tip of a glove fingertip.

13. The system of claim 11, wherein the tip of the structure is located adjacent a pad of a glove fingertip.

14. The system of claim 11, wherein the tip of the structure is located anywhere along the length of the structure.

15. The system of claim 1, wherein the substrate includes a switch to activate the positional device.

16. The system of claim 15, wherein the switch is located in the palm of a hand.

17. The system of claim 1, wherein the sensor is an optical tracking device.

18. The system of claim 1, wherein the anatomical structure is a bony structure.

19. The system of claim 1, wherein the first circuit is adapted to calculate the global position of the point when the substrate moves in relation to the point.

20. The system of claim 1, wherein the positional device comprises a magnetic tracker.

21. The system of claim 1, wherein the positional device comprises a fiber optic device.

22. A method for determining a position of a point on an anatomical structure of a patient using a surgical navigation system, the method comprising the steps of:
providing a surgical navigation system;
mounting a substrate in a removable manner to an outer surface of a user's body, the substrate having a positional device and a sensor that can be detected by the surgical navigation system to determine a position of the sensor;
covering a fingertip of the user with a finger mounted structure, wherein the finger mounted structure is movable in relation to the sensor, and wherein the positional device is adapted to determine a relative position of the finger mounted structure with respect to the positional device;
placing the finger mounted structure on the point of the anatomical structure to be determined;
calculating the relative position of the finger mounted structure in relation to the positional device; and
determining a global position of the point by concatenating the position of the sensor and the relative position of the finger mounted structure.

23. The method of claim 22, wherein a circuit is provided for displaying the global position of the point on the anatomical structure.

24. The method of claim 22, wherein a tip of the finger mounted structure is placed on the point of the anatomical structure to be determined.

25. The method of claim 24, wherein the tip of the finger mounted structure is located adjacent a tip of the user's finger.

26. The method of claim 24, wherein the tip of the finger mounted structure is located adjacent a pad of the user's finger.

27. The method of claim 24, wherein the tip of the finger mounted structure is located anywhere along the length of the finger mounted structure.

28. The method of claim 22, wherein the finger mounted structure is attached to the substrate and the substrate comprises a glove that is sufficiently flexible to enable the finger mounted structure to reach a point on the anatomical structure that is obstructed from view.

29. The method of claim 22, wherein tactile feedback to the user aids the user in maneuvering the finger mounted structure so that a position of the finger mounted structure correlates to the point on the anatomical structure.

30. The method of claim 22, wherein the outer surface of the user's body is a hand, and wherein the substrate comprises a flexible glove and the finger mounted structure is a fingertip of the flexible glove.

31. The method of claim 22, wherein the finger mounted structure comprises a finger mounted pointer.

32. The method of claim 31, wherein the finger mounted pointer includes a depressible tip.

33. The method of claim 32, wherein depressing the depressible tip activates the positional device.

34. The method of claim 33, wherein the depressible tip includes a transducer for activating the positional device when a defined pressure value is met.

35. The method of claim 32, wherein the depressible tip is placed on the point of the anatomical structure to be determined.

36. The method of claim 22, wherein the substrate includes a switch to activate the positional device.

37. The method of claim 36, wherein the switch is located on the palm of a hand.

38. The method of claim 22, wherein the user may utilize a second tool, and wherein the concurrent use saves the user time.

39. The method of claim 38, wherein the position of the point is determined at the same time the second tool is being used.

40. The method of claim 22, further comprising the steps of making an incision in a patient's body containing the anatomical structure, and reaching through the incision with the finger mounted structure to touch the point of the anatomical structure.

41. The method of claim 40, wherein the incision has a length less than 10 centimeters.

42. The method of claim 40, wherein the incision has a length less than 5 centimeters.

43. The method of claim 40, wherein the incision has a length between about 2.5 centimeters and about 5 centimeters.

44. The method of claim 40, wherein the incision is made in a region of a knee of the patient's body.

45. The method of claim 40, wherein the incision is made in a region of a hip of the patient's body.

46. The method of claim 22, wherein the sensor is an optical tracking device.

47. The method of claim 22, wherein the anatomical structure is a bony structure.

48. The method of claim 22, wherein the anatomical structure is an organ.

49. The method of claim 22, wherein the positional device comprises a magnetic tracker.

50. The method of claim 22, wherein the positional device comprises a fiber optic device.

51. A system for determining a global position of an object, comprising:
a navigation system;
a substrate comprising a glove adapted to be mounted to an outer surface of a user's body;
a sensor attached to the substrate that can be tracked by the navigation system to determine a position of the sensor;
a positional device attached to the substrate;
a structure mounted to a finger of the glove, wherein the structure is movable in relation to the sensor and the structure is adapted to be placed adjacent to a point on the object, and wherein the positional device is adapted to determine a relative position of the structure in relation to the positional device; and
a first circuit for calculating a global position of the point on the object by concatenating the position of the sensor and the relative position of the structure.

52. The system of claim 51, wherein a second circuit is provided for displaying the global position of the point on the object.

53. The system of claim 51, wherein the substrate is sufficiently flexible to enable the structure to reach a point on the object that is obstructed from view.

54. The system of claim 51, wherein tactile feedback to the user aids the user in maneuvering the structure so that the position of the structure correlates to the point on the object.

55. The system of claim 51, wherein the finger of the glove is separated from other portions of the substrate.

56. The system of claim 51, wherein the structure comprises a pointer.

57. The system of claim 56, wherein the pointer includes a depressible tip.

58. The system of claim 57, wherein depressing the depressible tip activates the positional device.

59. The system of claim 58, wherein the depressible tip includes a transducer for activating the positional device when a defined pressure value is met.

60. The system of claim 57, wherein the position of the structure is a position of the depressible tip.

61. The system of claim 51, wherein the position of the structure is a position of a tip of the structure.

62. The system of claim 61, wherein the tip of the structure is located at a tip of the user's finger.

63. The system of claim 61, wherein the tip of the structure is located at a pad of the user's finger.

64. The system of claim 61, wherein the tip of the structure is located anywhere along the length of the structure.

65. The system of claim 51, wherein the substrate includes a switch to activate the positional device.

66. The system of claim 65, wherein the switch is located on the palm of a hand.

67. The system of claim 51, wherein the sensor is an optical tracking device.

68. The system of claim 51, wherein the positional device comprises a magnetic tracker.

69. The system of claim 51, wherein the positional device comprises a fiber optic device.

70. A method for determining a position of a point on an object using a surgical navigation system, the method comprising the steps of:
providing a surgical navigation system;
mounting a glove on a user's hand, the glove having a positional device that determines a position of a point on the object and a sensor that can be detected by the surgical navigation system to determine a position of the sensor;
disposing a finger mounted structure on a finger of the glove capable of communicating with the positional device to determine a relative position of the structure in relation to the positional device, wherein the finger mounted structure is movable in relation to the sensor;
placing the finger mounted structure on the point of the object to be determined; and
determining a global position of the point by concatenating the position of the sensor and the relative position of the structure.

71. The method of claim 70, wherein a circuit is provided for displaying the global position of the point on the object.

72. The method of claim 70, wherein the glove is sufficiently flexible to enable the finger mounted structure to reach a point on the object that is obstructed from view.

73. The method of claim 70, wherein tactile feedback to the user aids the user in maneuvering the finger mounted structure so that a position of the finger mounted structure correlates to the point on the object.

74. The method of claim 70, wherein the finger mounted structure comprises a finger mounted pointer.

75. The method of claim 74, wherein the finger mounted pointer includes a depressible tip.

76. The method of claim 75, wherein depressing the depressible tip activates the positional device.

77. The method of claim 76, wherein the depressible tip includes a transducer for activating the positional device when a defined pressure value is met.

78. The method of claim 75, wherein the depressible tip is placed on the point of the object to be determined.

79. The method of claim 70, wherein a tip of the finger mounted structure is placed on the point of the object to be determined.

80. The method of claim 79, wherein the tip of the finger mounted structure is located adjacent a tip of the user's finger.

81. The method of claim 79, wherein the tip of the finger mounted structure is located adjacent a pad of the user's finger.

82. The method of claim 79, wherein the tip of the finger mounted structure is located anywhere along the length of the finger mounted structure.

83. The method of claim 70, wherein the user may utilize a second tool, and wherein the concurrent use saves the user time.

84. The method of claim 83, wherein the position of the point is determined at the same time the second tool is being used.

85. The method of claim 70, wherein the sensor is an optical tracking device.

86. The method of claim 70, wherein the positional device comprises a magnetic tracker.

87. The method of claim 70, wherein the positional device comprises a fiber optic device.

88. An apparatus for determining a position of a point on an anatomical structure, comprising:
a surgical navigation system;
a glove adapted to be mounted on a hand of a user;
a sensor attached to the glove that can be tracked by the surgical navigation system to determine a position of the sensor;
a magnetic tracker attached to the glove;
a structure comprising a magnetic sensor mounted to a finger of the glove, wherein the magnetic sensor is movable in relation to the sensor and the magnetic sensor is adapted to be placed adjacent to a point on the anatomical structure, and wherein the magnetic tracker determines a relative position of the magnetic sensor;
a first circuit for calculating a global position of the point on the anatomical structure by concatenating the position of the sensor and the relative position of the magnetic sensor.

89. The apparatus of claim 88, wherein the glove is sufficiently flexible to enable the structure to reach a point on the anatomical structure that is obstructed from view.

90. The apparatus of claim 88, wherein tactile feedback to the user aids the user in maneuvering the structure so that a position of the structure correlates to a point on the anatomical structure.

91. The apparatus of claim 88, wherein the magnetic sensor is mounted on a tip of the structure, and wherein the tip is maneuvered by the user adjacent the point on the anatomical structure to be determined.

92. The apparatus of claim 91, wherein the tip of the structure is located adjacent a tip of a user's finger.

93. The apparatus of claim 91, wherein the tip of the structure is located adjacent a pad of the user's finger.

94. The apparatus of claim 91, wherein the tip of the structure is located anywhere along the length of the structure.

95. The apparatus of claim 88, wherein the structure comprises a pointer mounted on a finger of the glove, and the magnetic sensor is disposed adjacent the pointer.

96. The apparatus of claim 95, wherein the pointer includes a depressible tip.

97. The apparatus of claim 96, wherein depressing the depressible tip activates the magnetic tracker.

98. The apparatus of claim 97, wherein the depressible tip includes a transducer for activating the magnetic tracker when a defined pressure value is met.

99. The apparatus of claim 96, wherein the depressible tip of the structure is maneuvered by the user adjacent the point on the anatomical structure to be determined.

100. The apparatus of claim 88, wherein the sensor is an optical tracking device.

101. A method for determining a position of a point on an anatomical structure through a small incision opening using a surgical navigation system, wherein the point is obstructed from the incision, the method comprising the steps of:
provanding a surgical navigation system;
mounting a substrate in a removable manner to an outer surface of a user's body;
covering a tip of the user's finger with a finger mounted pointer having a rigid tip, the finger mounted pointer being capable of communicating with an external positional device mounted on the substrate, the external positional device being associated with a sensor mounted on the substrate that can be detected by the surgical navigation system, and wherein the finger mounted pointer is movable in relation to the sensor;
manipulating the finger mounted pointer so that the rigid tip is in contact with the point to be determined;
determining the relative position of the finger mounted pointer in relation to the sensor with the external positional device;
determining the global position of the sensor; and
determining the global position of the point by concatenating the relative position of the finger mounted pointer and the global position of the sensor.

102. The method of claim 101, further comprising the step of displaying the global position of the point on the anatomical structure.

103. The method of claim 101, wherein the substrate comprises a flexible glove.

104. The method of claim 101, wherein tactile feedback to the user aids the user in maneuvering the finger mounted pointer so that a position of the rigid tip correlates to the point to be determined.

105. The method of claim 101, wherein the finger mounted pointer includes a depressible tip.

106. The method of claim 105, further comprising the step of depressing the depressible tip to activate the positional device.

107. The method of claim 106, wherein the depressible tip includes a transducer for activating the positional device when a defined pressure value is met.

108. The method of claim 105, wherein the depressible tip comprises the rigid tip of the finger mounted pointer.

109. The method of claim 101, wherein the rigid tip of the finger mounted pointer is located adjacent a tip of the user's finger.

110. The method of claim 101, wherein the rigid tip of the finger mounted pointer is located adjacent a pad on the user's finger.

111. The method of claim 101, wherein the rigid tip of the finger mounted pointer is located anywhere along the length of the finger mounted pointer.

112. The method of claim 101, wherein the user may utilize a second tool, and wherein the concurrent use saves the user time.

113. The method of claim 112, wherein the position of the point is determined at the same time the second tool is being used.

114. The method of claim 101, wherein the sensor is an optical tracking device.

115. The method of claim 101, wherein the anatomical structure is a bony structure.

116. The method of claim 101, wherein the anatomical structure is an organ.

117. The method of claim 101, wherein the positional device comprises a magnetic tracker.

118. The method of claim 101, wherein the positional device comprises a fiber optic device.

119. The method of claim 101, wherein the small incision is made in a patient's body containing the anatomical structure.

120. The method of claim 119, wherein the small incision opening is less than 10 centimeters in length.

121. The method of claim 119, wherein the small incision opening is less than 5 centimeters.

122. The method of claim 119, wherein the small incision opening is between about 2.5 centimeters and about 5 centimeters.

123. The method of claim 119, wherein the small incision is made in a region of a knee of the patient's body.

124. The method of claim 119, wherein the small incision is made in a region of a hip of the patient's body.

* * * * *